(12) United States Patent
Jacobs

(10) Patent No.: US 7,816,090 B2
(45) Date of Patent: Oct. 19, 2010

(54) MULTIPLE IMMUNOCHEMISTRY ASSAYS ON AN ELEMENT

(75) Inventor: Merrit N. Jacobs, Fairport, NY (US)

(73) Assignee: Ortho-Clinical Diagnostics, Inc., Rochester, NY (US)

( * ) Notice: Subject to any disclaimer, the term of this patent is extended or adjusted under 35 U.S.C. 154(b) by 321 days.

(21) Appl. No.: 11/621,797

(22) Filed: Jan. 10, 2007

(65) Prior Publication Data

US 2008/0166740 A1 Jul. 10, 2008

(51) Int. Cl.
*G01N 33/53* (2006.01)
(52) U.S. Cl. ............... 435/7.1; 435/7.5; 435/7.92; 435/7.93; 435/7.94; 435/7.95; 435/960; 435/969; 435/971; 435/973
(58) Field of Classification Search ............... 435/7.1, 435/7.5, 7.92, 7.93, 7.94, 7.95, 960, 969, 435/971, 973
See application file for complete search history.

(56) References Cited

U.S. PATENT DOCUMENTS

| | | | |
|---|---|---|---|
| 4,258,001 A | | 3/1981 | Pierce et al. |
| 4,270,920 A | * | 6/1981 | Kondo et al. ............ 436/170 |
| 4,670,381 A | | 6/1987 | Frickey et al. |
| 4,997,772 A | | 3/1991 | Sutton et al. |
| 5,620,860 A | | 4/1997 | Jacobs et al. |
| 5,641,860 A | | 6/1997 | Park et al. |
| 5,763,158 A | | 6/1998 | Bohannon |
| 5,843,691 A | * | 12/1998 | Douglas et al. ............ 435/14 |
| 5,885,526 A | * | 3/1999 | Chu ........................ 422/56 |
| 6,403,383 B1 | | 6/2002 | Casterlin et al. |
| 2005/0214161 A1 | | 9/2005 | Gupta |
| 2008/0182341 A1 | * | 7/2008 | Lu et al. ................. 436/526 |

FOREIGN PATENT DOCUMENTS

| | | |
|---|---|---|
| EP | 0747702 | 12/1996 |
| WO | WO 93/22679 | 11/1993 |

OTHER PUBLICATIONS

Gosling, Immunoassays, Oxford University Press, 2000, pp. 7-15.
Randox Laboratories Ltd., Overview of Evidence®, Copyright Randox Laboratories, Aug. 2002.

* cited by examiner

*Primary Examiner*—Bao-Thuy L Nguyen
(74) *Attorney, Agent, or Firm*—Todd J. Burns

(57) ABSTRACT

A method of analyzing a sample for one or more analytes of interest includes: providing an element having a base layer; a layer containing streptavidin; a spreading layer, wherein the streptavidin may or may not be in the spreading layer; providing immunocomponents and labeled immunoreactants which may be in the spreading layer or may be combined with the sample; dispensing the sample, and optionally the immunocomponents and a labeled immunoreactant onto the spreading layer at three or more areas, wherein each center of the three or more areas is substantially equidistance to the center formed by the three or more areas, and wherein each area contacts an adjacent area such that wash fluid flow in any direction will contact sample; washing the sample and label by directing the wash fluid at the center formed by the three or more areas, whereby the wash fluid equally flows over each of the three or more areas; and taking a measurement at each three or more areas to determine the presence or concentration of the one or more analyte. In a preferred embodiment, the element is a dry slide used on a diagnostic analyzer.

17 Claims, 2 Drawing Sheets

MULTIPLE IMMUNOCHEMISTRY ASSAYS ON AN ELEMENT

BACKGROUND OF THE INVENTION

The present invention relates to multiple immunochemistry assays on a single element. In particular, the present invention relates to a dry slide containing multiple assays used in a diagnostic analyzer.

Known diagnostic analyzers include clinical chemistry analyzers such as the Vitros® 5,1 FS, sold by Ortho-Clinical Diagnostics, Inc. All such analyzers are collectively called diagnostic analyzers. These diagnostic analyzers can use dry slides, such as those described in U.S. Pat. Nos. 4,258,001, 4,670,381, and 4,997,772, all of which are incorporated by reference in their entireties.

Slides contain an antigen or antibody reactive to the analyte of interest. The various structures of antigen or antibody anchoring in the immune complexes are described in Gosling, *Immunoassays*, Oxford University Press, 2000, pages 7-15, incorporated herein by reference. A patient sample (e.g., serum or urine) is deposited onto the slide having the label already on the slide. A short incubation follows which enables the analyte being measured to be captured, a portion of the element so deposited with sample is washed to remove uncomplexed labeled immunoreactant and to also add an activator, such as peroxide. A further incubation follows. Thereafter, a portion of the washed portion is read several times with a measurement device as it is incubated further, such as a densitometer or reflectometer to determine the rate of color development, and this rate is compared to calibrated results that are predictive of the concentration of the analyte—e.g., DGXN, PHYT or CRP.

As described above, it is known in the field of immunoassays using dried test elements, that uncomplexed labeled immunoreactants (i.e., antigen or antibody) need to be separated and removed from bound or complexed labeled immunoreactants, prior to detection. This is done by applying, after the sample is added, a wash liquid to the test element after the complexing reaction has occurred, to cause separation of the free labeled immunoreactants from those that are bound. Such separation, in theory, leaves a volume in the test element in which the bound labeled immunoreactants can be read free of the interference of the uncomplexed ones that are now washed away. The process is exemplified by U.S. Pat. Nos. 5,620,860 and 5,641,860, both of which are incorporated by reference in their entireties.

Such immunoassays test elements are typically constructed to test for only a single analyte. Such a construction inherently slows down the throughput of an analyzer by requiring a different test element for each assay desired.

For the foregoing reasons, there is a need for an immunochemistry assay element that is capable of supporting more than one assay.

SUMMARY OF THE INVENTION

The present invention is directed to meeting the need for an immunoassay test element capable of supporting more than one assay, particularly on a dry slide.

One aspect of the invention is directed to a method of analyzing a sample for one or more analytes of interest. The method includes: providing an element having a base layer; a layer containing streptavidin; a spreading layer, wherein the streptavidin may or may not be in the spreading layer; providing immunocomponents and labeled immunoreactants which may be in the spreading layer or may be combined with the sample; dispensing the sample, and optionally the immunocomponents and a labeled immunoreactant onto the spreading layer at three or more areas, wherein each center of the three or more areas is substantially equidistance to the center formed by the three or more areas, and wherein each area contacts an adjacent area such that wash fluid flow in any direction will contact sample; washing the sample and label by directing the wash fluid at the center formed by the three or more areas, whereby the wash fluid equally flows over each of the three or more areas; and taking a measurement at each three or more areas to determine the presence or concentration of the one or more analyte. In a preferred embodiment, the element is a dry slide used on a diagnostic analyzer.

Further objects, features and advantages of the present invention will be apparent to those skilled in the art from detailed consideration of the preferred embodiments that follow.

DETAILED DESCRIPTION OF PREFERRED EMBODIMENTS

Figure 1:
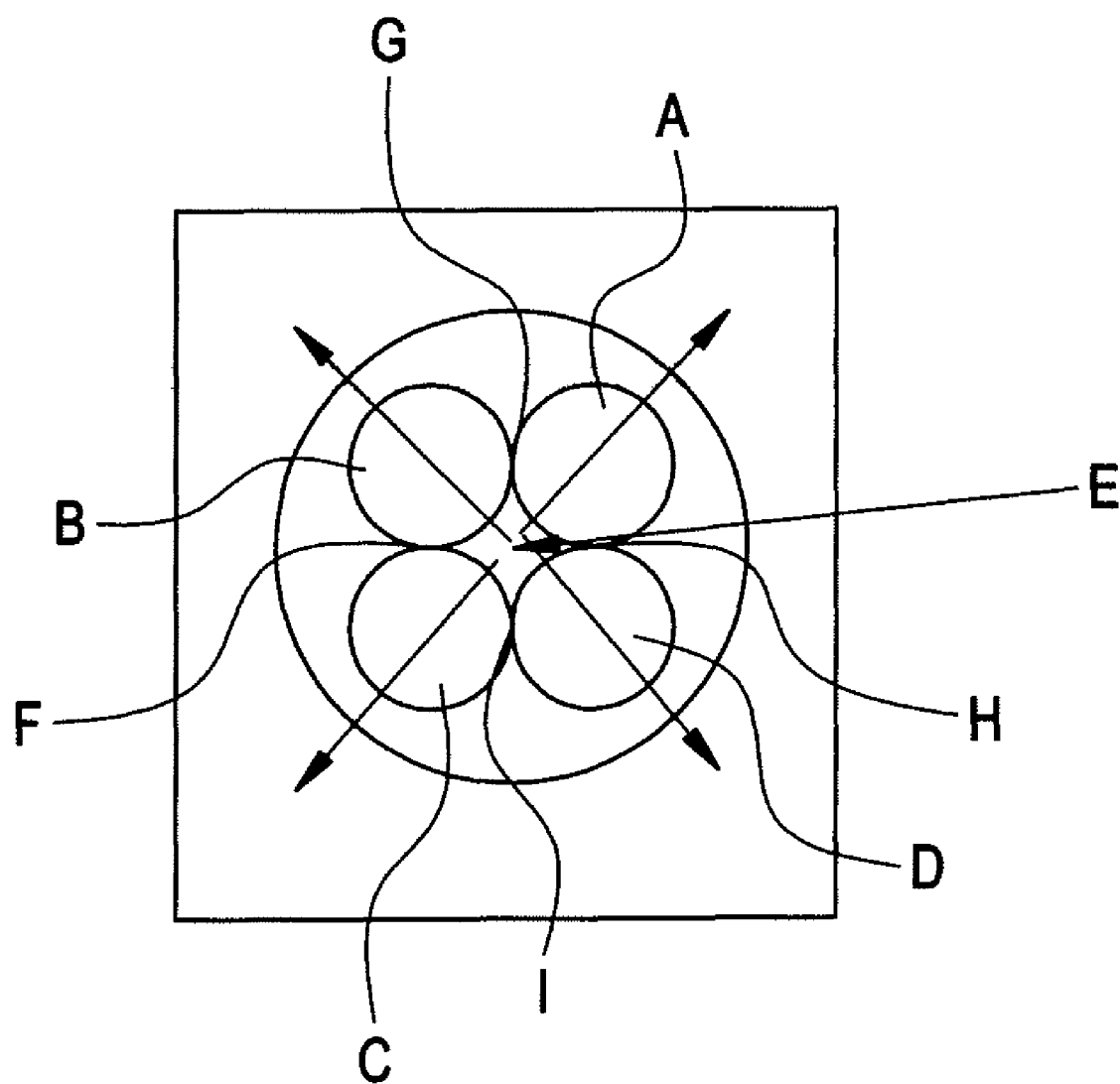
FIG. 1 is a schematic diagram of a slide having four assays arranged around a center point where wash fluid is directed.

The present invention is directed to an immunoassay element that allows multiple assays to be performed on a single element. One advantage of such a format is that it allows a "menu" of different analytes to be measured on the same element. For example, an infectious screening menu commonly used in blood donor screening will commonly test for HIV, Hepatitis A, Hepatitis B and Hepatitis C. Prior to the present invention, blood donor screening required large, e.g., 96 well, microtiter plates that had the same analyte performed in all wells. Thus, to simply screen for these four diseases would require four microtiter plates. If all the wells in the plates are not used, this leads to considerable waste and expense. With the present invention, a single donor can be tested on a single element as opposed to numerous microtiter plates.

Another advantage of the present invention is the ability to have a calibrator (e.g., reference) on the same element. For example, in one embodiment of the present invention, the element can have multiple numbers of the same assay on a single element. One of the assay locations on the element can include a calibrator or reference. This provides an increased element stability, since the calibrator will be subject to the same storage and use conditions as the actual assays on the element.

The present invention provides a panel of assays on the same element, e.g., slide structure. This improves the system throughput without a substantial investment in new hardware. It also reduces the cost per test because it only would use one test element for multiple results.

As used herein, "labeled immunoreactant" means any labeled antibody or antigen that is used to detect a target analyte, such as an antigen or antibody, whether the assay be via a competitive assay in which a target antigen, for example, competes with a labeled version of the antigen, or a sandwich assay in which a target antigen, for example, forms a sandwich between a capture antibody and a labeled antibody (the labeled immunoreactant). The label in turn can be any useful detectable direct or indirect indicator, e.g., a fluorophor or an enzyme such as HRP, respectively. As used herein, "immunocomponents" refers to all other reactive species, e.g., capture or linking antibodies or antigens, biotin, etc. employed, except for the labeled immunoreactant.

An example of preparing such a multi assay element is as follows:

(1) A base layer made of a clear material such as polyester or Mylar is provided.

(2) A buffer layer is then provided on the base layer.

(3) A support and absorbing layer made of gelatin or a polymer with a leuco dye is provided. Antioxidants are mixed in with the dye to slow down the age related spontaneous conversion of the dye from white to colored.

(4) A spreading layer is prepared containing polystyrene beads held together with a water soluble latex adhesive.

(5) Included in the spreading layer or as a separate layer below the spreading layer are streptavidin coated beads.

Applications of these layers is preferably applied to the entire element. However, the layers can also be applied to each of the areas of the element that will contain an assay. Now each different assay is prepared by one of the embodiments described below.

The process for completing the test element and for assaying an analyte on such a test element is as follows. Depending on the assay to be performed the labeled immunoreactant and immunocomponents (the components for N different assays) can be applied in several different embodiments described below. (There will be at least N different locations spotted onto the element. More than N different locations will be spotted if multiple spots of the same assay are performed, such as to verify calibration or control):

1. All the immunocomponents and labeled immunoreactants for each N assay are homogeneously coated in the spreading layer during manufacture. The sample(s) are then spotted onto the element (e.g., the spreading layer of a dry slide).

2. N immunocomponents and labeled immunoreactants above are coated in N different layers for each N assay resulting in an X/Y but not Z uniformity. N samples are then spotted onto the element (e.g., spreading layer of a dry slide).

3. All components are separately coated to form N different assays. The N different assays are then joined on the test element during the manufacturing process. The process of joining may be through splicing the separate components together. Sample(s) are then spotted onto the element (e.g., spreading layer of a dry slide).

4. All immunocomponents for the N assays are mixed with the sample and the sample is subdivided into N aliquots. Labeled immunoreactant, e.g., HRP label, for each analyte is added to each of the N aliquots. Each of these mixtures of sample and labeled immunoreactant is then spotted on the slide in N locations.

5. The sample is aliquoted into N containers and mixed separately with the immunocomponents for each N assay and also the labeled immunoreactant, e.g. HRP. This mixture is spotted on the element (e.g., spreading layer of a dry slide) in N different locations. This is the most preferred embodiment.

6. A combination of embodiments 1 and 5. All N immunocomponents for N different assays are coated homogenously into the spreading layer. The sample is aliquoted into N containers and then it is mixed with the labeled immunoreactants for each N assay and then spotted onto the element in at least N separate locations. The drawback of this embodiment is that it may loose specificity of the assays since both ends of the sandwich will not be linking to portions of the analyte we are trying to measure.

For example, attached covalently to the streptavidin coated beads in the entire element or the areas for each assay are immobilized anti-antigen antibodies, such as anti-phenobarbital antibody or anti-TSH antibodies, or immobilized antigens. Preferably, these are added with the sample such as in Embodiment 5, described above. The labeled immunoreactant, e.g., antigen peroxidase conjugate which competes with the target analyte in the sample for binding sites on the immobilized antibodies or antigens. This labeled immunoreactant ideally should be included as a known amount with the sample and applied to the element at the same time as the sample. This first assay on the slide is labeled as A in FIG. 1

Another type of immobilized anti-antigen antibodies or antigens is deposited adjacent to the first assay and immobilized on the streptavidin. The same continues for a third and fourth assay each containing a different immobilized anti-antigen antibodies or antigens. These are labeled in FIG. 1 as B, C and D, respectively. These can be a panel of assays, such as Hepatitis A, B, C and HIV or a cardiac panel, such as Troponin, CKMB Myoglobin and proBNP or a fertility panel HCG, LH, FSH. There is no limit to the number of assays that can be included on each element. The only limiting factors are that the center of each assay spot must be equidistant from the wash center as will be explained in more detail below and that the sample spots must all touch so that there is no dry spreading layer between sample where wash fluid can preferentially flow. This contact between samples is shown by reference letters F, G, H, I in FIGS. 1 and 2. Thus, an element could contain 3, 4, 5, 6, etc. assays arranged around a central wash spot E as shown in FIG. 1. Thus, on a single element, it is possible to perform multiple different assays on a single sample, or different assays on multiple samples. While the above description has been described as each assay being different, it is entirely possible that each assay spot is for the same analyte. That is, each immobilized anti-antigen antibody or immobilized antigen is the same. This would allow multiple samples to be assayed for the same analyte. However, a single sample could be run on the same assays and placed in all four locations enabling the system to average the results and provide a more reliable estimate or a calibration or control fluid can be spotted along with the patient spot to calibrate each result. The same would be true when only two assays are requested, only then both assays would be run in duplicate on the slide and deposited from the same tip in the same metering cycle. The inclusion of multiple assays on a single element would allow one or more of the additional spots to contain a control or calibrator fluid.

In practice, a drop of patient sample is metered on each assay on the element and evenly distributed by the spreading layer. The analyte in the sample competes with the labeled immunoreactant for a limited number of binding sites during the first incubation capture (for competitive assays) or links between the SAC bond and the anti-antigen and the label bond through an anti-antigen for the sandwich assays.

A short incubation follows which enables the analyte being measured to be captured, a portion of the element so deposited with sample is washed to remove uncomplexed labeled immunoreactant. An additional wash is carried out containing an activator, such as a peroxide and further incubation follows.

Thereafter, a portion of the washed portion is read several times with a measurement device as it is incubated further, such as a densitometer or reflectometer to determine the rate of color development, and this rate is compared to calibrated results that are predictive of the concentration of the analyte—e.g., CKMB or Myglobin.

The labeled immunoreactant can be attached to the analyte of interest for competitive assays, or to an antibody for sandwich assays, either process being of use in this invention.

The present invention provides a method of performing multiple assays on a single element where the sample and label are placed on the element in three or more areas, e.g., four or more areas. An important feature is that the center of the three or more areas is substantially equidistance to the center formed by the combined three or more areas and that there are no dry wedges or gaps of spreading layer between the spots.

In the preferred example where there would be four locations or areas, there is four metering events to place sample at each of the four locations plus one "dual" wash. Dual meaning that the first wash is a bound free separation with no activator, e.g., peroxidase, added so there is no activation step, while in the second wash the activation chemical is also present. Prior to the present invention, no design has been able to deal with all of the issues associated with fabrication, integration on the analyzer and maintaining an effective wash process with multiple assays or different samples on the same slide.

An important feature of the present invention is to structure the metering process on the element so that each one of the four sample and label spots can be deposited on the slide during the same metering cycle or in subsequent metering cycles. This is enabled by the insensitivity of this method to incubation time on the slide because of the very fast binding that will occur with streptavidin coated (SAC) type system.

Figure 2:
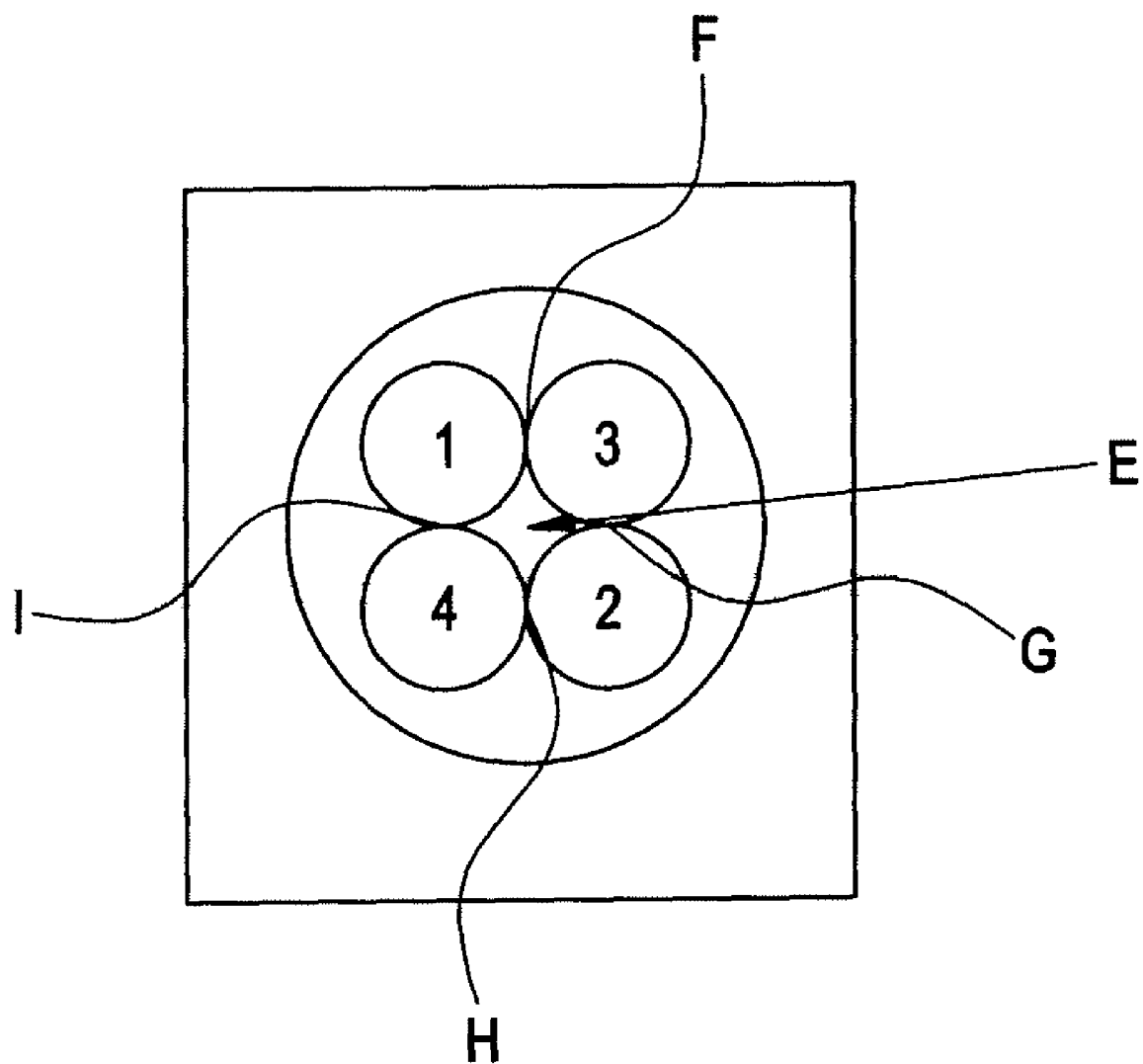
FIG. 2 is a schematic diagram of a slide having four assays and the order in which sample and optionally labeled immunoreactant and other immunocomponents are applied.

Washing is an important part of the invention, because it is necessary that each assay on the element receives the same amount of wash fluid to ensure complete and equal separation of the unbound labeled immunoreactant from the bound labeled immunoreactant. A ramped wash as described in U.S. Pat. No. 5,620,860, incorporated herein by reference in its entirety, enables the wash in the center point E of the group of assays as shown in FIG. 2. This wash in the center point of the group of assays maintains wash fluid in all assay areas of the element (even if only one result is required) which allows the wash to work with the multiple assay spots on the element. If the center spot of the assays is not surrounded by assays in all directions, the result would be a short circuiting of the wash process where the wash fluid would preferentially flow into dry spreading layer where an assay is not present. As both FIG. 1 and FIG. 2 clearly show, wash fluid that is deposited in the center of the assays, would necessarily encounter assay as the wash fluid flows away from the center towards to the periphery of the element. This will require the wash fluid to equally contact and interact with each of the assays on the element, thus ensuring a consistent wash for all assays.

FIG. 2 depicts one preferred metering order that could be used. As shown in FIG. 2, the diagonal metering method reduces the fluid interaction during the metering process allowing the sample (and optionally the immunocomponents and labeled immunoreactant) fluid to be absorbed before adding sample (and optionally immunocomponents and labeled immunoreactant) to adjacent assays. As explained above, after metering a first incubation is performed to allow, e.g., the antigen and labeled immunoreactant to competitively attach to the anchored antibody. The element is then metered with another wash fluid and again incubated to allow color development of the leuco dye. The color development can be rate measured or measured at an endpoint. Both of these techniques are well known in the art. The element, e.g., slide may be ideally read using an image capture device for example using a CCD as the capture element in a reflectometer to remove the positional sensitivity between the read and the metering processes.

Advantages of using multiple assays on a single slide include the following:

Improved throughput;

Reduced cost per test;

Capability of reluctant analysis using an internal reference that could reduce issues associated with stability which in turn allows an inherently less expensive analyzer and lower quality manufacturing process to have acceptable performance.

The basic test structure can be performed on existing diagnostic platforms with some minor modifications at most.

The test element can be any suitable structure including a variety of solid supports including test tube walls, plastic cups, beads, plastic balls and cylinders and papers and plastic balls. In a particularly preferred embodiment, the test element is a slide such as that used in the Vitros® brand analyzer. Such slides are described in U.S. Pat. No. 4,258,001, which is incorporated by reference in its entirety.

The present invention can also be used in blood donor screening assays because of the batch nature of that business, i.e., a microtiter plate is used instead of a slide element. The multi-test approach coupled with the potential of doing a reference or control on each slide helps fulfill the usual requirements for blood banking associated with throughput, reliability and cost. The current process for blood banking is a microtiter plate, which always has calibrators or controls on the same plate. The multi-assay element of the present invention (e.g., 3 assays and three controls) has the capability of doing half of the panel of assays required for blood banking on each slide and have reference values for each assay on the same slide along with the result to assure that the test is correct or provide greater assurance which is necessary in this type of testing environment. It is desirable to have all the results for a particular patient or in this case, unit of blood come out at the same time but this is not possible with the current microtiter plate design. Also if one only needs to run 10 results on a plate the rest of the plate can be wasted. This is substantial cost since each cell on the plate costs about three dollars.

The incorporation of an internal reference in the multi-assay element, has the potential to enable this technology to move to reduced or "factory" calibration. Factory calibration opens up applications in the veterinary and point-of-care (POC) fields because calibration requires a higher skill level than just running the analyzer. This is because calibration requires getting the fluid in the correct order, some times reconstitution is required, and there are several steps that are needed to be done by the operator. Then the calibration needs to be checked/verified. In a veterinary and POC field often they do not have the time or training needed to do calibration so an automated or factor calibration enables testing to be done in these markets where otherwise it would have to be moved to a central lab.

The method for washing a multi-assay slide element can be implemented by a computer program, having computer readable program code, interfacing with the computer controller of the analyzer as is known in the art.

It will be apparent to those skilled in the art that various modifications and variations can be made to the compounds, compositions and processes of this invention. Thus, it is intended that the present invention cover such modifications and variations, provided they come within the scope of the appended claims and their equivalents.

The disclosure of all publications cited above are expressly incorporated herein by reference in their entireties to the same extent as if each were incorporated by reference individually.

I claim:

1. A method of analyzing a sample for one or more analytes of interest, comprising:
   providing an element having
      a base layer;
      a layer containing streptavidin; and
      a spreading layer, wherein the streptavidin may or may not be in the spreading layer;
   providing immunocomponents and labeled immunoreactants which may be in the spreading layer or may be combined with the sample;
   spotting the sample onto the spreading layer at three or more areas, and optionally the immunocomponents and a labeled immunoreactant, wherein each center of the three or more areas is substantially equidistant to the center formed by the three or more areas, and wherein each area contacts an adjacent area such that wash fluid flow in any direction will contact sample;
   washing the sample and the labeled immunoreactant by directing a wash fluid at the center formed by the three or more areas, whereby the wash fluid flows away from the center towards the periphery of the element and equally flows over each of the three or more areas; and
   taking a measurement at each of the three or more areas to determine the presence or concentration of the one or more analytes.

2. The method of analyzing a sample for one or more analytes of interest as claimed in claim 1, wherein the immunocomponents comprise a capture or linking antibody or antigen.

3. The method of analyzing a sample for one or more analytes of interest as claimed in claim 1, wherein the element comprises a dry slide used on a diagnostic analyzer.

4. The method of analyzing a sample for one or more analytes of interest as claimed in claim 1, wherein the three or more areas are four areas having one of hepatitis A, hepatitis B, hepatitis C and human immunodeficiency virus assay.

5. The method of analyzing a sample for one or more analytes of interest as claimed in claim 1, wherein the three or more areas include a cardiac panel which includes Troponin, CKMB, Myoglobin and proBNP.

6. The method of analyzing a sample for one or more analytes of interest as claimed in claim 1, wherein the three or more areas include a fertility panel which includes HCG, FSH and LH.

7. The method of analyzing a sample for one or more analytes of interest as claimed in claim 1, wherein the three or more areas are four areas and further comprising an incubation period before the wash step.

8. The method of analyzing a sample for one or more analytes of interest as claimed in claim 1, wherein the immunocomponents and labeled immunoreactant are in the spreading layer before the sample is dispensed.

9. The method of analyzing a sample for one or more analytes of interest as claimed in claim 8, wherein the immunocomponents comprise capture or linking antibodies/antigens.

10. The method of analyzing a sample for one or more analytes of interest as claimed in claim 1, wherein the immunocomponents for each different analyte are in different layers.

11. The method of analyzing a sample for one or more analytes of interest as claimed in claim 10, wherein the immunocomponents comprise the capture or linking antibodies/antigens.

12. The method of analyzing a sample for one or more analytes of interest as claimed in claim 1, wherein the immunocomponents for each different assay are mixed with the sample and the sample is then divided into three or more aliquots, and further wherein a labeled immunoreactant for each analyte being detected/measured is added to one of the aliquots.

13. The method of analyzing a sample for one or more analytes of interest as claimed in claim 12, wherein the immunocomponents comprise capture or linking antibodies/antigens.

14. The method of analyzing a sample for one or more analytes of interest as claimed in claim 1, wherein the sample is separated into different aliquots and immunocomponents and labeled immunoreactant for each different assay are mixed with the sample in a different aliquot.

15. The method of analyzing a sample for one or more analytes of interest as claimed in claim 14, wherein the immunocomponents comprise capture or linking antibodies/antigens.

16. The method of analyzing a sample for one or more analytes of interest as claimed in claim 1, wherein the immunocomponents for each different analyte are in the spreading layer before the sample and labeled immunoreactant are added.

17. The method of analyzing a sample for one or more analytes of interest as claimed in claim 16, wherein the immunocomponents comprise capture or linking antibodies/antigens.

* * * * *